United States Patent [19]

Holl et al.

[11] 4,201,474
[45] May 6, 1980

[54] VARIABLE ANGLE OF INCIDENCE REFLECTOMETER WITH A CONTINUOUS READ OUT

[75] Inventors: Herbert B. Holl; Thomas G. Roberts, both of Huntsville, Ala.

[73] Assignee: The United States of America as represented by the Secretary of the Army, Washington, D.C.

[21] Appl. No.: 931,235

[22] Filed: Aug. 7, 1978

[51] Int. Cl.² ............................................. G01N 21/48
[52] U.S. Cl. ................................. 356/369; 250/224; 356/445
[58] Field of Search .............................. 356/445–448, 356/369; 250/224

[56] References Cited
U.S. PATENT DOCUMENTS

| | | | |
|---|---|---|---|
| 2,406,166 | 8/1946 | Scott | 356/448 |
| 3,402,631 | 9/1968 | Potter | 356/369 |
| 3,603,690 | 9/1971 | Hard | 356/445 X |

Primary Examiner—John K. Corbin
Assistant Examiner—Bruce Y. Arnold
Attorney, Agent, or Firm—Nathan Edelberg; Robert P. Gibson; James T. Deaton

[57] ABSTRACT

An instrument (reflectometer) for continuously measuring the reflectance properties of materials as a function of the angle of incidence in which a sample and a mirror are mounted on a rotating platform in such a manner that, as the angle of incidence on the sample is varied, the reflected radiation is always incident on a detector which is fixed with respect to the rotating platform. The angle of incidence on the sample is measured and used to drive an axis of an X-Y recorder. The angle of incidence on the mirror is measured and used to correct the detected signal for any errors introduced by the properties of the mirror. This corrected signal is then used to drive the other axis of the X-Y recorder to produce a plot of the reflection coefficients vs angle of incidence for the sample. For fixed angles of incidence on the sample the detector can be moved to produce a plot of the diffused reflections as a function of the angular deviation from the specular angle. For this purpose the position of the detector is measured and used to drive the x-axis of the X-Y recorder. The input radiation is generally obtained from a laser and the instrument is supplied with polarizers or a polarization rotator as desired.

6 Claims, 5 Drawing Figures

VARIABLE ANGLE OF INCIDENCE REFLECTOMETER WITH A CONTINUOUS READ OUT

BACKGROUND OF THE INVENTION

The current interest in laser radar systems has created a need for determining the reflectance properties of the many materials from which the targets for such systems are made. These targets are generally very complicated and are of such a size that the optical radar cross sections are almost impossible to measure in the far field. Therefore, much effort has been expended to develop computer codes for calculating these cross sections. Part of the necessary input data for these codes consist of the detailed reflectance properties of the materials from which the surfaces of the targets are made. To obtain these surface properties an instrument which might be called a reflectometer is used. These instruments utilize the laser of interest to the optical radar system and measure the reflected energy from the surface of material samples as the angle of incidence is varied. The angle of incidence is usually varied by rotating the sample, but this causes the angle for specular reflection to change by twice the angle through which the sample is rotated, and the detector has to be re-aligned for each angle of incidence.

Therefore, it is an object of this invention to provide an instrument which avoids the necessity for realigning the detector and thereby provides for a continuous recording of the specular reflectance as a function of the angle of incidence.

Another object of this invention is to provide a device which records reflectance as a function of the angular deviation of the detector from the specular angle for any fixed angle of incidence.

Still another object of this invention is to place a mirror on a rotating platform at a dihedral angle from the sample with the axis of rotation being at the apex of the dihedral angle formed by the mirror and sample.

Still another object of this invention is to provide a device in which a potentiometer type indicator is used to measure the angle of incidence.

A further object of this invention is to provide a device in which the reflected light beam from the mirror is always aligned on the detector.

A still further object of this invention is to provide a reflectometer with a continuous read out.

Other objects and advantages of this invention will be obvious to those skilled in this art.

SUMMARY OF THE INVENTION

This device includes a motor housing and a rotating platform that is rotatably mounted relative thereto. A sample holder and mirror are mounted on the rotating platform in such a manner that radiation reflected from the mirror always falls on a detector that is mounted on the motor housing. The detector is adjustably mounted relative to the housing and has means for fixing it in particular positions relative to the housing. The motor housing also has means thereon for measuring the angle of incidence of a laser beam on the sample, the angle of incidence of the reflected beam on the mirror, and the position of the detector with respect to the invariant direction of the light reflected from the mirror. A preprogrammed computer means is provided for receiving the detected signal, and the computer means is used to correct the detected signal for the effects introduced by the mirror in accordance with the angle of incidence of the mirror. Polarizers and a polarization rotator can be used with the invention to polarize the light from the source. The data produced by the device is presented on recorder means such as an X-Y recorder or on an electronic scope when the sample being tested is rotated through small angles rapidly or stepwise.

DESCRIPTION OF THE PREFERRED EMBODIMENT

Figure 1:
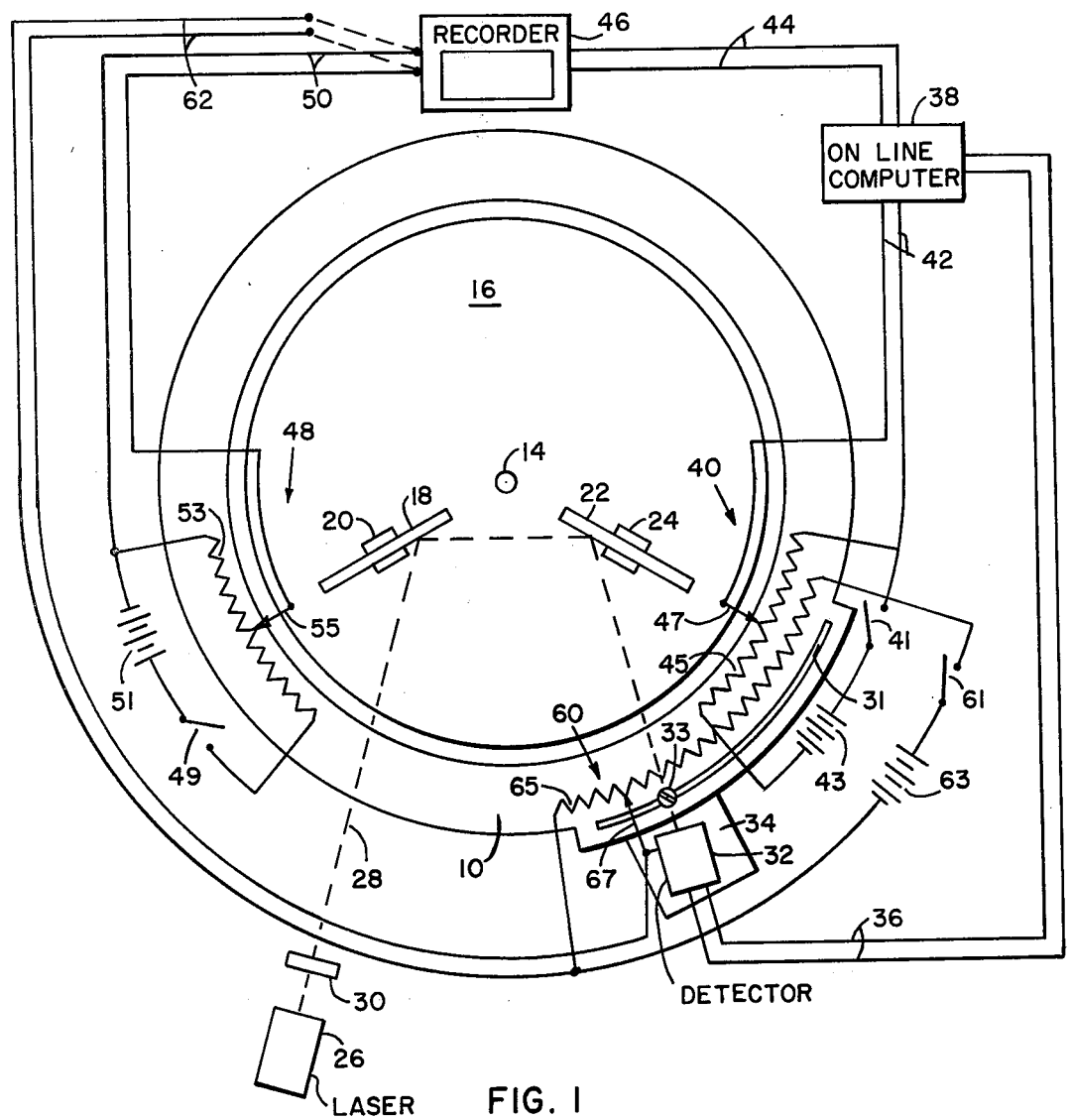
FIG. 1 is a schematic top plan view of the variable angle incidence reflectometer in accordance with this invention.
Figure 2:
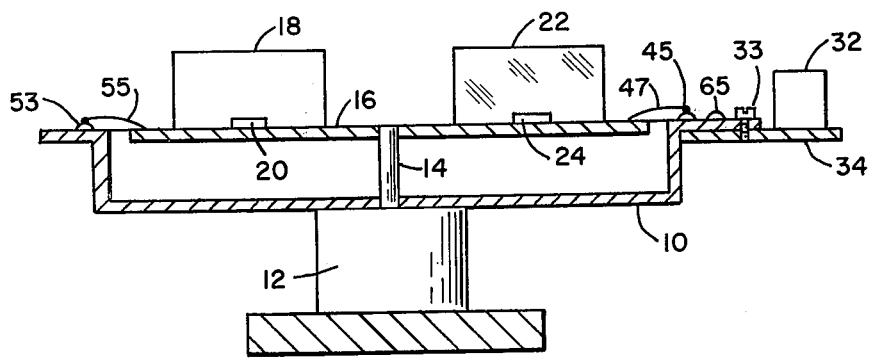
FIG. 2 is a sectional view of the body and rotating platform of the reflectometer in accordance with this invention and also illustrating the sample and mirror arrangement with the detector.
Figure 3:
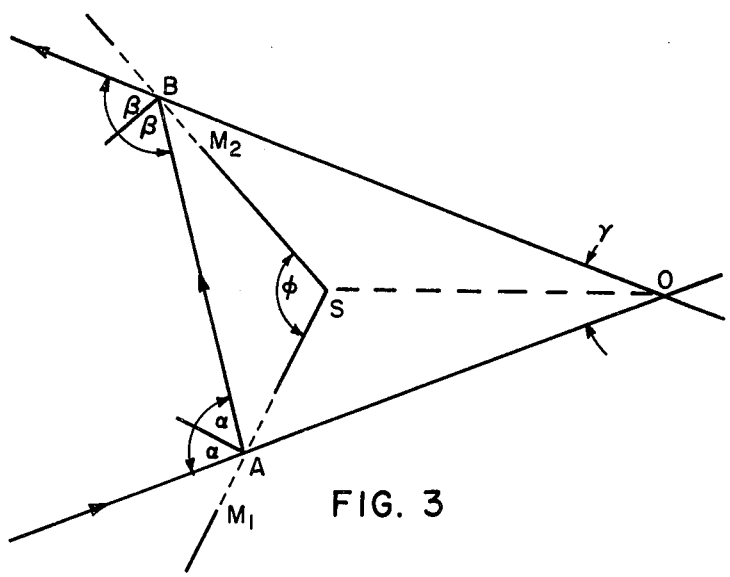
FIG. 3 is an optical diagram of a dihedral sample holder-mirror system.

Referring now to the drawing, the variable angle of incidence reflectometer includes a housing 10 (See FIG. 2) with an electric motor 12 secured thereto and having a drive shaft 14. Motor 12 is a motor that rotates slowly or one that is a stepping type motor. Motor 12 drives shaft 14 which is connected to platform 16 in a conventional manner for rotating platform 16. A test sample 18 is mounted on platform 16 in a conventional manner by mounting means 20. A mirror 22 is also mounted on platform 16 in a conventional manner by mounting means 24. Mirror 22 is mounted at a dihedral angle to sample 18 with the axis of rotation being at the apex of the dihedral angle formed by the mirror and sample. The apex of the dihedral angle coincides with the axis of rotation of shaft 14 (See FIG. 1). Laser 26 is physically mounted in a conventional manner for illuminating sample 18 with illuminating light rays 28. A polarizer 30 can be used to polarize light rays 28 if desired or a ¼ wave plate can be used as a polarization rotator. The illumination of light rays 28 from sample 18 is reflected onto mirror 22 and from mirror 22 onto detector 32 that is of conventional structure. Detector 32 is mounted on structure 34 that is adjustably mounted in any conventional manner to housing 10 such as by slot 31 and clamp screw 33. Detector 32 is positioned for receiving the reflected light rays from mirror 22, as motor 12 rotates shaft 14 to rotate and vary the angle of incidence of light rays 28 on sample 18. As the angle of incidence is varied, mirror 22 continues to reflect the light from sample 18 onto detector 32. This is the case due to the mounting of sample 18 and mirror 22 on the dihedral angle. This relationship of the reflection of the light beam is illustrated in the diagram of FIG. 3. (Sample 18 is illustrated as being located at $M_1$ and mirror 22 is illustrated as being located at $M_2$). When platform 16 is rotated about axis 14 which coincides with axes S of FIG. 3, the angle of incidence and therefore the amount of light reflected varies, but since $\alpha+\beta=$constant, the angles $\alpha$ and $\beta$ change in such a manner that the direction of the beam leaving the mirror is invariant to the rotation as illustrated in FIG. 3.

Figure 4:
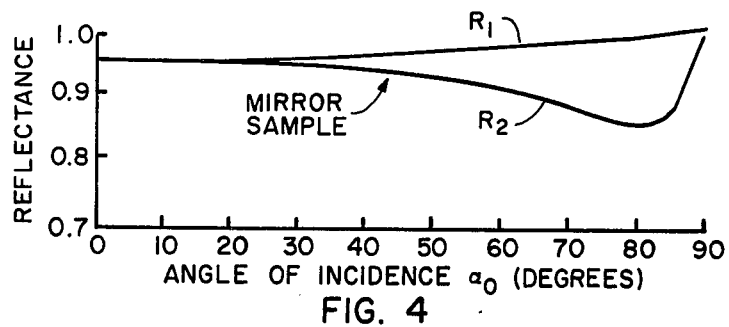
FIG. 4 is a plot of the reflective coefficient for a mirror as a function of the angle of incidence.
Figure 5:
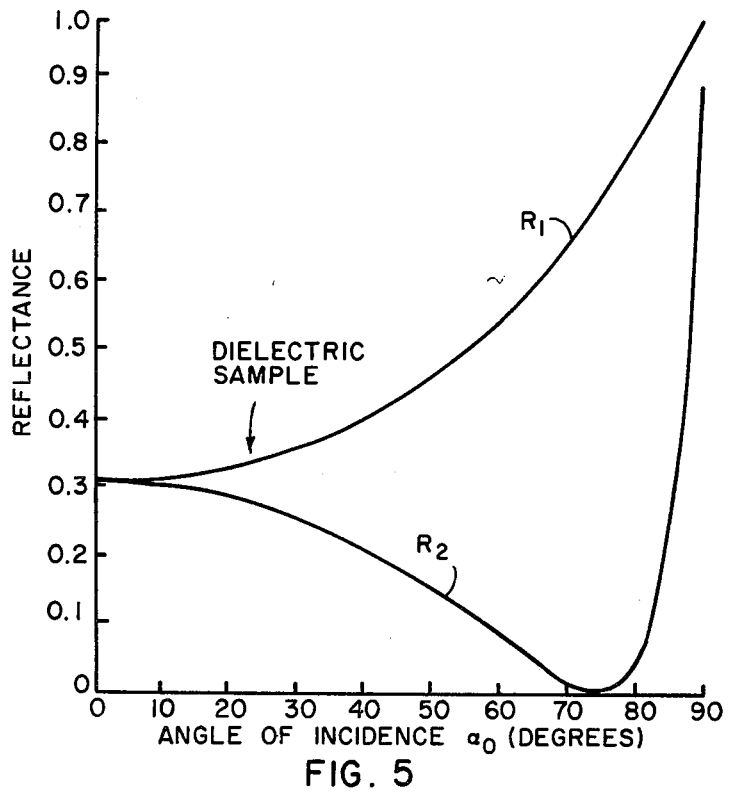
FIG. 5 is a plot of the reflective coefficient for a dielectric reflector as a function of the angle of incidence.

Since a mirror is not a perfect reflector, correction must be made in order for the output signal to be that which is reflected from sample 18. This is accomplished by potentiometer and computer arrangement. That is, the output from detector 32 is connected by leads 36 to on-line computer 38. On-line computer 38 also receives signals from potentiometer 40 by leads 42 to signal the on-line computer the measured angle of incidence for the light or mirror 22. Depending upon the particular angle of incidence of the mirror, computer 38 is preprogrammed to divide the output signal received by leads 36 by an appropriate factor and thereby correct for the mirror imperfections. As seen in FIG. 4, the reflection properties of a mirror vary as the angle of incidence and also in accordance with the polarization of the light. After the particular characteristics of mirror 22 are determined in a conventional manner, these characteristic curves are programmed into on-line or mini computer 38 to make the appropriate corrections. Output 44 from computer 38 is used to drive one axis of recorder 46. The other axis of recorder 46 receives a signal from potentiometer 48 through leads 50; therefore, recorder 46 plots out a curve of the reflectance properties of sample 18 which will look similar to that illustrated in FIG. 4 or that illustrated in FIG. 5. The particular shape of the curve will depend upon the particular material of which sample 18 consists. That is, if sample 18 is a metallic mirror, the curves will look like that of those of FIG. 5. The $R_1$ and $R_2$ curves in FIGS. 4 and 5 represent perpendicularly polarized light and parallelly polarized light. If the light from the laser source is not polarized, then the curves will be represented by $R = \frac{1}{2} (R_1 + R_2)$. The preprogramming of computer 38 in order to correct for the imperfections of the mirror is preprogrammed in accordance with the desired curves on recorder 46. That is, if $R_1$ curves are desired, computer 38 is preprogrammed for $R_1$ curves or if $R_2$ curves are desired, computer 38 is programmed in accordance with $R_2$ or if R curves are desired of unpolarized light, computer 38 is preprogrammed with R curve. If it is desired to switch from one curve to another, computer 38 is preprogrammed with R, $R_1$, and $R_2$ curves and the computer is provided with means for switching to the desired curve in accordance with the light being used to illuminate the sample.

Potentiometer 40 has a switch 41 for interconnecting biasing means 43 across base 45 and a sliding contact 47 is mounted on base 16 to vary the resistance of potentiometer 40 as platform 16 is rotated. Also, potentiometer 48 has a switch 49 for connecting biasing source 51 across base 53 of the potentiometer and a sliding contact 55 is mounted on platform 16 and is rotated as platform 16 is rotated to vary the resistance of potentiometer 48.

If this invention is desired to be used to measure the diffused reflection from the same sample, then light detector 32 is adjustably mounted through support 34 relative to base 10 to where base 34 can be moved through an arc of movement relative thereto and also fixed in a particular position when being used for measuring the angle of incidence. This mounting is of conventional structure such as illustrated at 31, 33. Also, potentiometer 60 is provided which includes switch 61 for connecting biasing means 63 across base 65 of the potentiometer and a sliding contact 67 is mounted on support 34 for detector 32 to vary the resistance of potentiometer 60 as light detector 32 is moved by moving base 34 relative to base 10. Potentiometer 60 has leads 62 that are interchanged for leads 50 of potentiometer 48 to provide a signal to recorder 46 to cause the recorder to plot a curve of a diffused reflection from the sample.

In operation, the primary use of this device is to measure the reflective properties of a sample as a function of the angle of incidence. When used for this purpose, laser 26 is turned on and motor 12 is started to turn platform 16 and vary the angle of incidence which changes the amount of light energy reflected by sample 18. Also, potentiometers 40 and 48 are turned on by closing switches 41 and 49 and potentiometer 48 is used to measure the angle of incidence of the light beam on the sample. The output through leads 50 of potentiometer 48 drive one axes of X-Y recorder or electronic scope 46. Potentiometer 40 is used to measure the angle of incidence of light beam on the mirror. This measurement is fed to on-line computer 38 by leads 42 where it is used with a curve like that of FIG. 4 that has been preprogrammed into computer 38 to decide the correction factor needed for correcting the detector signal for the particular angle of incidence. The output of detector 32 is also fed to on-line computer 38 where it is divided by the appropriate correction factor preprogrammed into computer 38. Then the output from on-line computer 38 is fed by leads 44 to recorder 46 for driving the other axis of X-Y recorder or electronic scope 46. Now, as platform 16 is rotated, a curve which gives the reflectance as a function of the angle of incidence on the sample is obtained on recorder 46. The curve is generally plotted for light polarized in a particular direction—say parallel to the plane of incidence. The plane of polarization can then be rotated 90° through the use of polarizer 30 or a ¼ wave plate and the measurement repeated so as to obtain a complete characterization of the sample. These two polarizations give $R_1$ and $R_2$ curves as similar to those depicted in FIGS. 4 and 5. Also, computer 38 has to be set to make its correction in accordance with the particular polarization of the light used to illuminate the sample.

If it is desired to measure the diffused reflection from sample 18, then this instrument has leads 50 of potentiometer 48 disconnected from recorder 46 and leads 62 of potentiometer 60 connected to recorder 46. Leads 62 of potentiometer 60 have a signal thereon which indicates the position of detector 32 relative to base 10 and this signal is used to drive this axis of recorder 46. Now, by moving detector 32 to either side (first one side, then the other) of the position of specular reflection, the magnitude of the diffused reflections is plotted as a function of the angle of the detector as measured from the angle of specular reflection. For these measurements, only detector 32 is moved. That is, platform 16 is stationary when this measurement is made. Of course, these measurements can be done for the desired components of the polarization and at the particular angle of incidence desired.

I claim:

1. A reflectometer comprising a base, a platform rotatably mounted relative to said base, a motor mounted relative to said base and said platform for rotating said platform relative to said base, a sample and a mirror mounted on said platform at a dihedral angle relative to the axis of rotation of said platform, means for illuminating said sample, a light detector mounted on said base relative to said mirror for receiving reflected light therefrom, a first means mounted relative to said base and said platform and having output leads connected for indicating the angle of incidence of the light beam from said light means on said sample, said output leads of said first means being connected to a first axis of a recorder, a second means mounted relative to said base and said platform and having output leads connected for indicating the angle of incidence of the light beam from the mirror, said output leads of said second means being connected to a computer means, said light detector having output leads connected to said computer means, said computer means being preprogrammed to correct for imperfections of said mirror, said computer means correcting the signal from the light detector utilizing the angle of incidence of the mirror information received from said second means and the preprogrammed correction and providing the corrected signal to the other axis of the recorder for driving the other axis of the recorder.

2. A reflectometer as set forth in claim 1, wherein said light means is a laser light source, and having a polarizer means between the laser light source and the sample for polarizing the laser light.

3. A reflectometer as set forth in claim 1, wherein said detector is adjustably mounted relative to said base, and having a third means mounted relative to said base and said detector, said third means having output leads for indicating the position of said detector relative to said base, and said output leads of said third means being interchangeable with the output leads from said first means for driving said first axis of said recorder.

4. A reflectometer as set forth in claim 3, wherein said second and third means are potentiometers, said recorder is an X-Y recorder, and said computer means is an on-line computer.

5. A reflectometer as set forth in claim 1, wherein said first and second means are potentiometers and said computer means is an on-line computer.

6. A reflectometer as set forth in claim 5, wherein said recorder is an X-Y recorder.

* * * * *